United States Patent [19]

Ullrich et al.

[11] Patent Number: 5,248,830

[45] Date of Patent: Sep. 28, 1993

[54] ENANTIOSELECTIVE PREPARATION OF ACETYLENIC OR OLEFINIC SUBSTITUTED CYCLOALKENYL DIHYDROXYBUTYRATES AND 4-HYDROXY-TETRAHYDRO-PYRAN-2-ONES

[75] Inventors: John Ullrich, Audubon, Pa.; John R. Regan, Princeton, N.J.

[73] Assignee: Rhone-Poulenc Rorer Pharmaceuticals Inc., Collegeville, Pa.

[21] Appl. No.: 902,752

[22] Filed: Jun. 23, 1992

Related U.S. Application Data

[63] Continuation of Ser. No. 654,120, Feb. 11, 1991, abandoned, which is a continuation-in-part of Ser. No. 398,015, Aug. 24, 1989, Pat. No. 4,992,429.

[51] Int. Cl.$^5$ .............................................. C07C 49/225
[52] U.S. Cl. ...................................... 568/329; 568/330; 568/306
[58] Field of Search ................................. 568/329, 330

[56] References Cited

U.S. PATENT DOCUMENTS

| | | | |
|---|---|---|---|
| 3,860,653 | 1/1975 | Hellerbach | 568/329 |
| 3,890,397 | 6/1975 | Rees et al. | 568/329 |
| 3,974,157 | 8/1976 | Shetty et al. | 568/329 |
| 4,118,558 | 10/1978 | Turk et al. | 568/329 |
| 4,576,964 | 3/1986 | Eggler et al. | 514/546 |
| 4,684,396 | 8/1987 | Clough et al. | 514/184 |

FOREIGN PATENT DOCUMENTS 61-268646 11/1986 Japan .................................. 568/329

OTHER PUBLICATIONS

Coubere et al, Chem. Abst., vol. 80, #120,628j (1974).
Feiser et al., "Reagents for Organic Synthesis", pp. 72 & 137 (1967).

Primary Examiner—James H. Reamer
Attorney, Agent, or Firm—Raymond S. Parker, III; Martin F. Savitzky

[57] ABSTRACT

Disclosed are intermediates and a process of making an anticholesterolemic compound of the formula

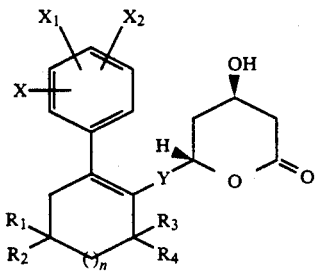

the corresponding ring-opened hydroxy acids derived therefrom and pharmaceutically acceptable salts thereof.

2 Claims, No Drawings

ENANTIOSELECTIVE PREPARATION OF ACETYLENIC OR OLEFINIC SUBSTITUTED CYCLOALKENYL DIHYDROXYBUTYRATES AND 4-HYDROXY-TETRAHYDRO-PYRAN-2-ONES

This is a continuation of copending application Ser. No. 07/654,120 filed on Feb. 11, 1991, now abandoned, which is a continuation-in-part of U.S. application Ser. No. 398,015 filed Aug. 24, 1989, now U.S. Pat. No. 4,992,429.

BACKGROUND OF THE INVENTION

1. Field of the Invention

The present invention relates to a process for preparing pharmaceutical compounds which are useful in reducing serum cholesterol in mammals.

More particularly, the invention relates to intermediates and a process for preparing (4R,6S)-6-[2-[2-substituted phenyl)-4,4,6,6-tetrasubstituted cycloalken-1-yl]eth(an)(en)yn-1-yl]-4-hydroxy-3,4,5,6-tetrahydro-pyran-2-one, and the corresponding ring opened hydroxy acids derived therefrom.

Hypercholesterolemia is known to be one of the major risk factors of cardiovascular disease such as arteriosclerosis. There are known agents that are active antihypercholesterolemic that function by limiting cholesterol biosynthesis by inhibiting the enzyme, HMG-CoA reductase. HMG-CoA is a substance which controls the rate at which cholesterol is synthesized in mammalian liver. The significance of such compounds has been widely recognized for several years, e.g.. Breslow, et al., Biochim. Biophys. Acta, 398, 10 (1975); Betheridge, et al., Brit. Med. J., 4,500 (1975); Brown, et al., Scientific American, 48 Nov. (1984).

2. Reported Developments

Many workers are investigating various compounds having antihypercholesterolemic activity. Illustrative references directed to such compounds and/or process of making them follow:

U.S. Pat. No. 4,681,893 to B. D. Roth pertains to trans-6-[2-(3- or 4-carboxamido-substituted pyrrol-1-yl)-alkyl]-4-hydroxypyran-2-ones useful as hypocholesterolemic agents.

U.S. Pat. No. 4,668,699 to Hoffman, et al. discloses semi-synthetic analogs of compactin and mevinolin and the dihydro and tetrahdyro analogs thereof for antihypercholesterolemic application.

U.S. Pat. No. 4,282,155 to Smith, et al. is directed to 6(R)-[2-(8'-etherified-hydroxy-2',6'-dimethylpolyhydronaphthyl-1')ethyl]-4(R)-hydroxy-3,4,5,6-tetrahydro-2H-pyran-2-ones for inhibition of biosynthesis of cholesterol.

U.S. Pat. No. 4,567,289 relates to methyl, ethyl, n-propyl, 2-(acetylamino)ethyl, or 1-(2,3-dihydroxy)propyl ester of E-(3R,5S)-7-(4'-fluoro-3,3',5-trimethyl-[1,1'-biphenyl]-2-yl)-3,5-dihydroxy-6-heptenoic acid that are HMG-CoA reductase inhibitors.

U.S. Pat. No. 4,611,067 discloses a process for the preparation of HMG-CoA reductase inhibitors which contain a 4-hydroxy-3,4,5,6-tetrahydro-2H-pyran-2-one moiety.

Merck Sharp & Dohme's product MEVACOR® (Lovastatin is [1S-[1α(R*),3α,7β,8β(2S*,4S*),-8aβ]]1,2,3,7,8,8a-hexahydro-3,6-dimethyl-8-[2-(tetrahydro-4-hydroxy-6-oxo-2H-pyran-2-yl)ethyl]-1-napthalenyl-2-methylbutanoate is a cholesterol lowering agent isolated from a strain of *Aspergillus terreus*. After oral ingestion, lovastatin, which is an inactive lactone, is hydrolized to the corresponding β-hydroxy acid form. This is an inhibitor of 3-hydroxy-3-methylglutaryl-coenzyme A (HMG-CoA) reductase. This enzyme catalyses the conversion of HMG-CoA to mevalonate, which is an early and rate limiting step in the biosynthesis of cholesterol. MEVACOR® is reported to function well as a cholesterol reducing agent having relatively few side effects. There is, however, a continuing need for new compounds having improved efficacy with minimum side effects.

U.S. Pat. No. 4,863,957 discloses 3-hydroxy-3-methylglutarylcoenzyme A reductase inhibitors of the formula:

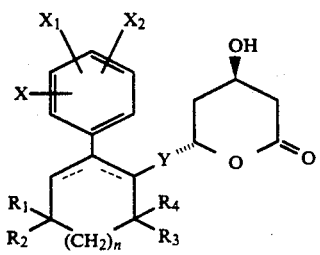

wherein:

Y is —CHR—, —CHRCHR—, —CHRCHRCHR—, OR —RC=CR—;

X, $X_1$ and $X_2$ are independently H, F, Cl, Br, OH, $CF_3$, alkyl, alkoxy, aryl, $NO_2$, NH(CO)R, $N(R)_2$, or $S(O)_mR$;

$R_1$ and $R_2$ are independently H, alkyl, aryl, OH, OR, F, Cl, or Br;

$R_3$ and $R_4$ are independently H or lower alkyl;

R is H or lower alkyl;

n is 0–2;

m is 0–2; and the dotted lines between carbons 1 and 2 or 2 and 3 in the cycloalkyl ring represent an optional double bond.

The process disclosed for synthesizing the above-shown compounds provides satisfactory yields of the racemic mixtures. However, the process lacks in the production of sufficient enantiomeric excess.

The present invention provides intermediates and a stereospecific synthetic process for making said intermediates useful in the preparation of pharmaceutical compounds.

In a further aspect the present invention also provides a convergent and enantiospecific synthesis of (4R,6S)-6-[2-[2-substituted phenyl)-4,4,6,6-tetrasubstituted cycloalken-1-yl]eth(an)(en)yn-1-yl]-4-hydroxy-3,4,5,6-tetrahydro-pyran-2-one, compounds useful in the treatment of hypercholesterolemia. The stereo synthesis provides an efficient method for the preparation of the target molecules with high enantiomeric excess starting from readily available materials.

SUMMARY OF THE INVENTION

The present invention provides compounds of formulae I, II and III:

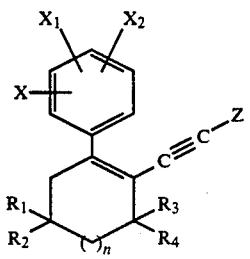

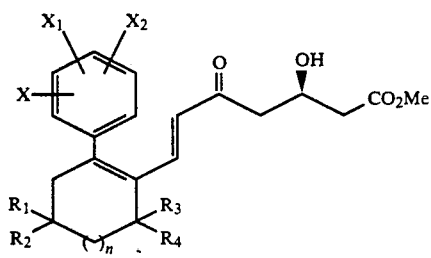

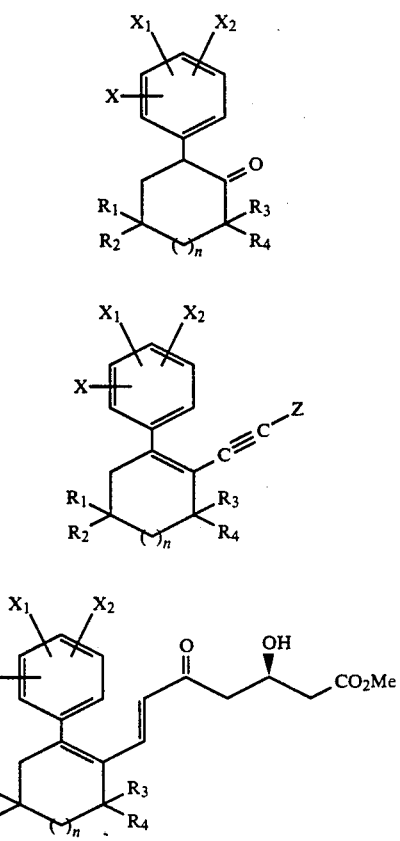

Formula I

Formula II

Formula III wherein

X, $X_1$ and $X_2$ are independently H, F, Cl, Br, OH, $CF_3$, alkyl, alkoxy, aryl, $NO_2$, NH(CO)R, $N(R)_2$ or $S(O)_m R$;

Z is trialkylsilyl;

$R_1$ and $R_2$ are independently H, alkyl, aryl, OR, F, Cl or Br;

R is H or lower alkyl;

$R_3$ and $R_4$ are independently H or lower alkyl, and $R_3$ and $R_4$ taken together can form a spirocyclic ring having 4 to 6 carbon atoms; and n is 0-2.

The invention also provides a method for the preparation of a compound of formula I

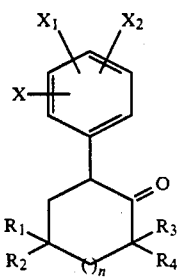

Formula I comprising converting a compound of the formula

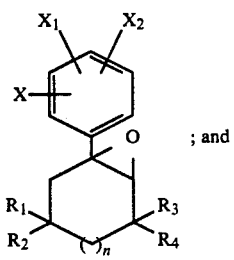

to a compound of the formula containing an oxirane

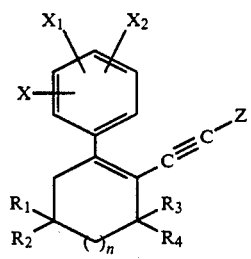

; and rearranging the formed oxirane to said compound of formula I, wherein X, $X_1$, $X_2$, R, $R_1$, $R_2$, $R_3$, $R_4$ and n are as defined above.

This inveniton further provides a method for the preparation of a compound of formula II

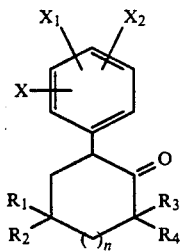

Formula II comprising: reacting a compound of formula I in the presence of an acetylene anion Formula I to obtain a compound of the formula

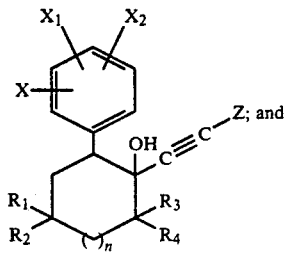

dehydrating said compound wherein X, $X_1$, $X_2$, R, $R_1$, $R_2$, $R_3$, $R_4$, n and Z are as defined above.

Still further, the invention provides a method for the preparation of a compound of formula III

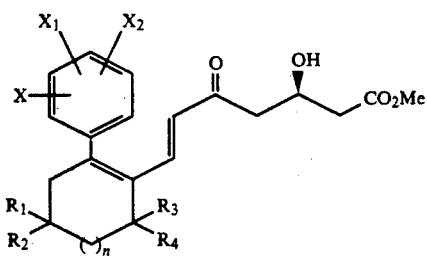

Formula III comprising: coupling a compound of the formula

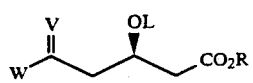

with a compound of the formula

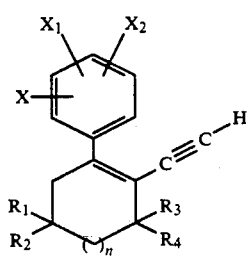

to obtain a compound of the formula

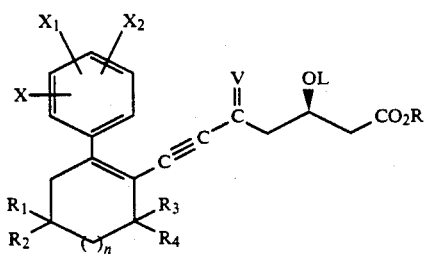

wherein
X, $X_1$ and $X_2$ are independently H, F, Cl, Br, OH, $CF_3$, alkyl, alkoxy, aryl, $NO_2$, NH(CO)R, $N(R)_2$ or $S(O)_mR$;
$R_1$ and $R_2$ are independently H, alkyl, aryl, OR, F, Cl or Br;
R is H or lower alkyl;
$R_3$ and $R_4$ are independently H or lower alkyl, and $R_3$ and $R_4$ taken together can form a spirocyclic ring having 4 to 6 carbon atoms;
n is 0-2;
W is a halogen;
V is O, S,

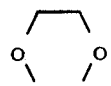

or $CO_2R$; and

L is an oxygen protecting group.

A preferred aspect of this invention relates to a process for the preparation of a compound of formula IV

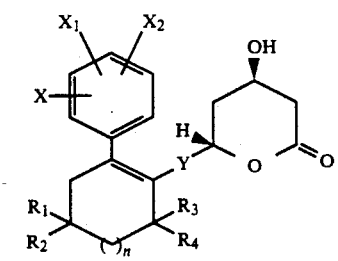

Formula IV wherein:
Y is —CHRCHR—, —RC=CR— or —C≡C—;
X, $X_1$, $X_2$, R, $R_1$, $R_2$, $R_3$ and $R_4$ are as defined above;
n is 0-2;
m is 0-2, its hydroxy acids; and pharmaceutically acceptable salts thereof comprising:
converting a 2-(substituted phenyl)-4,4,6,6-tetrasubstituted cycloalkene to a 2-(substituted phenyl)-4,4,6,6-tetrasubstituted cycloalkanone;
transforming the cycloalkanone to a 1-ethynyl-2-(substituted phenyl)-4,4,6,6-tetrasubstituted cycloalkene;
converting said cycloalkene to a methyl (3R)-3-(tert-butyldimethylsilyl)oxy-5-oxo-7-[2-(substituted phenyl)-4,4,6,6-tetrasubstituted cycloalken-1-yl]hept-6-yn-oate; and
converting the 5-oxo-hept-6-yn-oate derivative to a diol derivative and transforming the diol ester to obtain (4R,6S)-6-[2-[2-(substituted phenyl)-4,4,6,6-tetrasubstituted cycloalken-1-yl]eth(an)(en)yn-yl]-4-hydroxy-3,4,5,6-tetrahydropyran-2-one.

DETAILED DESCRIPTION OF THE INVENTION

As employed above and throughout the specification, the following terms, unless otherwise indicated, shall be understood to have the following meaning:

"Lower alkyl" means a saturated or unsaturated aliphatic hydrocarbon which may be either straight- or branched-chained containing from 1 to 4 carbon atoms.

"Alkyl" means a saturated or unsaturated aliphatic hydrocarbon which may be either straight- or branched-chained containing from about 1 to about 6 carbon atoms.

"Alkoxy" means an alkyl oxy group in which "alkyl" is as previously defined. Lower alkoxy groups are preferred which include methoxy, ethoxy, n-propoxy, i-propoxy, sec-propoxy and n-butoxy.

"Aryl" means an aromatic hydrocarbon radical having 6 to 10 carbon atoms. The preferred aryl groups are phenyl, substituted phenyl and naphthyl. The term "substituted" means "alkyl" substitution.

Pharmaceutically acceptable salts within the scope of the invention are those derived from the following acids: mineral acids such as hydrochloric acid, sulfuric acid, phosphoric acid and sulfamic acid; and organic acids such as acetic acid, citric acid, lactic acid, tartaric acid, malonic acid, methanesulfonic acid, ethanesulfonic acid, benzenesulfonic acid, p-toluenesulfonic acid, cyclohexylsulfamic acid, quinic acid, and the like. The corresponding acid addition salts comprise the following: hydrochloride, sulfate, phosphate, sulfamate, acetate, citrate, lactate, tartarate, malonate, methanesulfonate, ethanesulfonate, benzenesulfonate, p-toluenesulfonate, cyclohexylsulfamate and quinate, respectively.

The acid addition salts of the compounds of this invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Where the compound of the invention is in the ring-opened hydroxy acid form, base addition salts may be formed and are simply a more convenient form for use; and in practice, use of the salt form inherently amounts to use of the free acid form of the ring-opened hydroxy acid. The bases which can be used to prepare the base addition salts include preferably those which produce, when combined with the free acid, pharmaceutically acceptable salts, that is, salts whose cations are non-toxic to the animal organism in pharmaceutical doses of the salts, so that the beneficial hypocholesterolemic properties inherent in the free acid are not vitiated by side effects ascribable to the cations. Pharmaceutically acceptable salts within the scope of the invention are those derived from the following bases: sodium hydroxide, potassium hydroxide, calcium hydroxide, aluminum hydroxide, lithium hydroxide, magnesium hydroxide, zinc hydroxide, ammonia, ethylenediamine, N-methylglucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, tetramethylammonium hydroxide, and the like.

Metal salts of compounds of the present invention may be obtained by contacting a hydroxide, carbonate or similar reactive compound of the chosen metal in an aqueous solvent with the ring-opened hydroxy acid. The aqueous solvent employed may be water or it may be a mixture of water with an organic solvent, preferably an alcohol such as methanol or ethanol, a ketone such as acetone, an aliphatic ether such as tetrahydrofuran, or an ester such as ethyl acetate. Such reactions are normally conducted at ambient temperature but they may, if desired, be conducted with heating.

Amine salts of compounds of the present invention may be obtained by contacting an amine in an aqueous solvent with the ring-opened hydroxy acid. Suitable aqueous solvents include water and mixtures of water with alcohols such as methanol or ethanol, ethers such as tetrahydrofuran, nitriles such as acetonitrile, or ketones such as acetone. Amino acid salts may be similarly prepared.

The invention encompasses optical and stereoisomers of the compounds and mixtures thereof defined by the structural formula.

The general procedure for the synthesis of the present invention is illustrated in Scheme I while the detailed procedure is shown in Scheme II, wherein the radicals used correspond with those denoted in connection with formulae I, II, III and IV.

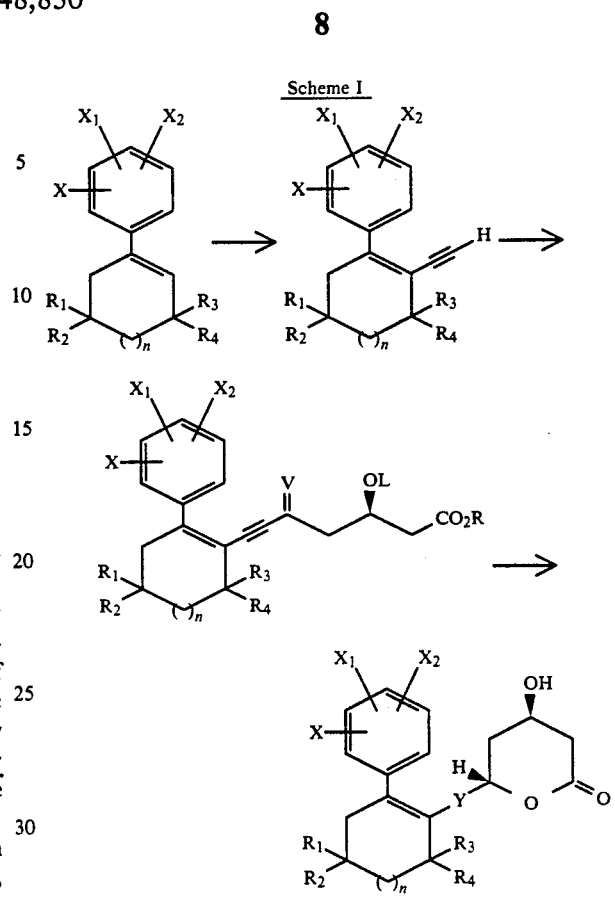

Scheme I

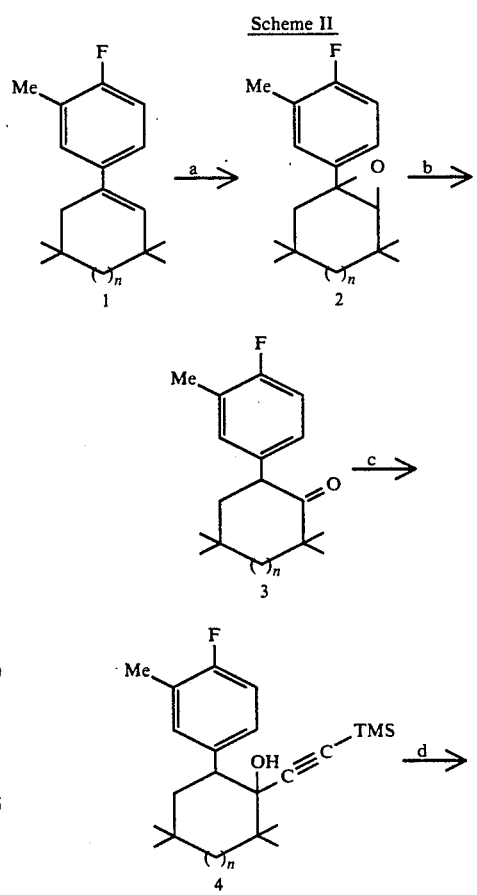

Scheme II

-continued
Scheme II

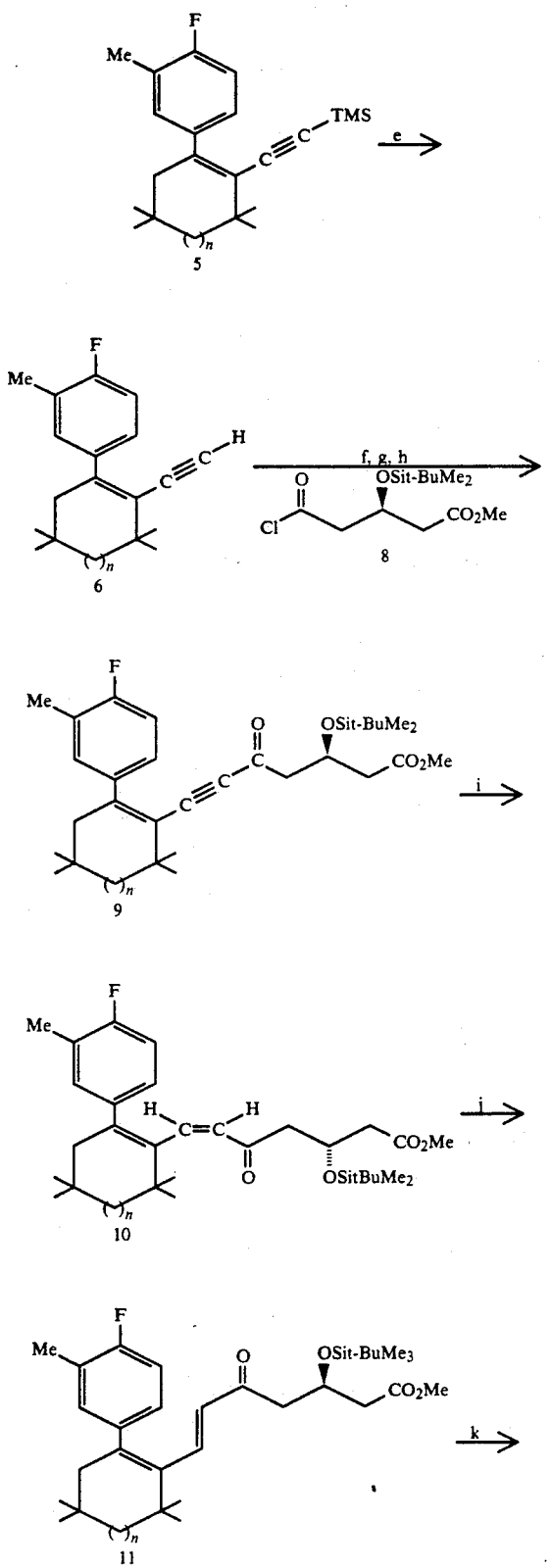

-continued
Scheme II

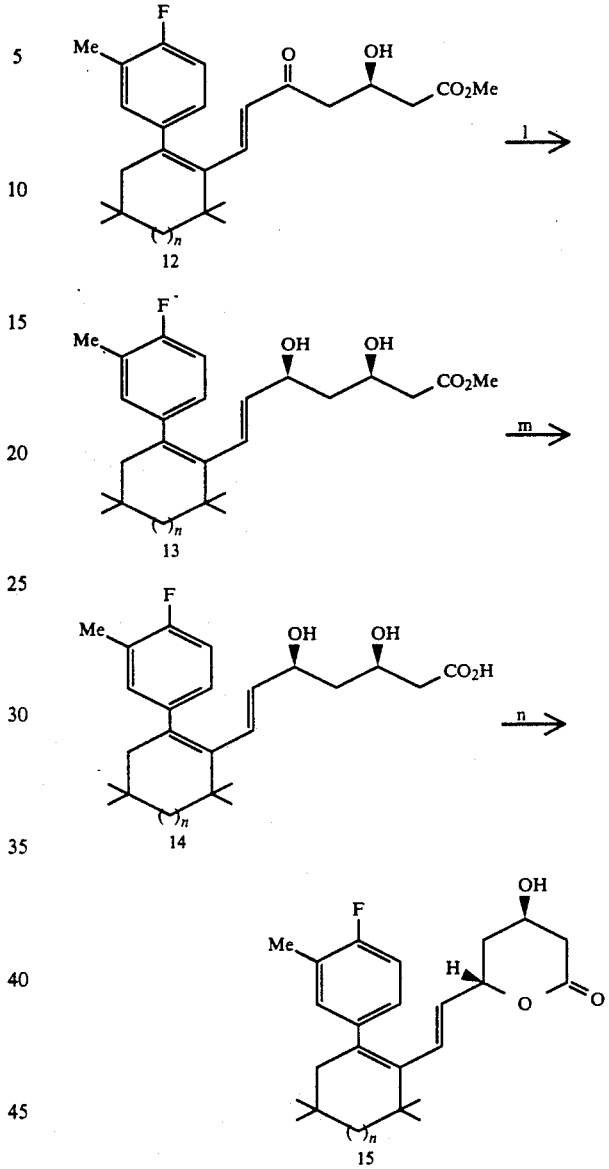

Reagents:
a. mCPBA, K₂HPO₄, CH₂Cl₂, 0° C. to RT;
b. BF₃·OEt₂, C₆H₆, 0° C. to RT;
c. TMS-acetylene, n-BuLi, THF, 0° C. to RT;
d. "Burgess Reagent" [MeO₂CN⁻SO₂N⁺Et₃], CH₃CN, reflux, 14 h;
e. (n-Bu)₄N⁺F⁻, AcOH, THF, 0° C. to RT;
f. n-BuLi, 0° C.;
g. MnI₂, −10° C.;
h. (3S)-4-methoxycarbonyl-3-(t-butyldimethylsilyl)oxybutanoyl chloride (8);
i. H₂, Pd(OH)₂, ca 20 psi, EtOAc;
j. I₂, (cat), Toluene, 60° C.;
k. HF/H₂O, CH₃CN;
l. Et₃B, MeOH, −10° C. THF, NaBH₄/THF (0.5M);
m. 10% NaOH, CH₃CN;
n. ClCO₂Et, TEA The following discussion refers to Scheme II, steps a through n, in describing the synthetic process of the present invention which comprises:

(a and b) Converting 2-(substituted phenyl)-4,4,6,6-tetrasubstituted cycloalkene by oxidation and rearrangement to a 2-(substituted phenyl)-4,4,6,6-tetrasubstituted cycloalkanone;

(c) Ethynylating said cycloalkanone by adding lithio trimethylsilyl-acetylene thereto;

(d and e) Dehydrating the hydroxy trimethylsilyl-acetylene and removing the trimethylsilyl group to obtain the 1-ethynyl-2-(substituted phenyl)-4,4,6,6-tetrasubstituted cycloalkene;

(f) Treating 1-ethynyl-2-(substituted phenyl)-4,4,6,6-tetrasubstituted cycloalkene to form the acetylenic anion;

(g and h) Adding said acetylenic anion with metalloalkyls, metallodialkyl amides, metalloamides, metallohydrides and metalloalkoxy species to a metal halide, said metal in said metal halide is selected from the group consisting of lithium, sodium, potassium, magnesium, manganese, zinc, boron, aluminum and cerium, and then to [3S]-4-methoxycarbonyl-3-(t-butyldimethylsilyl)-oxybutanoyl chloride to give methyl [3R]-7-[2-(substituted phenyl)-4,4,6,6-tetrasubstituted cycloalken-1-yl]-5-oxo-3-(t-butyldimethylsilyl)oxy-hept-6-yn-oate;

(i) Converting, via hydrogenation, said substituted heptynoate to methyl [3R]-7-(substituted phenyl)-4,4,6,6-tetrasubstituted cycloalken-1-yl]-5-oxo-3-(t-butyldimethylsilyl)oxy-hept-6-en-oate;

(j) Isomerizing said cis compound to its trans configuration;

(k) Removing the silyl ether to obtain a β-hydroxy keto-ester;

(l) Reducing said β-hydroxy keto-ester to the corresponding diol ester;

(m) Hydrolyzing the diol ester to obtain the diol acid; and (n) Lactonizing the diol acid to obtain (4R,6S)-[2-[2-(substituted phenyl)-4,4,6,6-tetrasubstituted cycloalken-1-yl]ethenyl]-4-hydroxy-3,4,5,6-tetrahydro-pyran-2-one.

Further details of the synthetic process follow, wherein the steps identified by letters a through n correspond with the steps a through n employed above.

(a and b) Conversion of said 2-(substituted phenyl)-4,4,6,6-tetrasubstituted cycloalkene is by peracid or peroxide oxidation; and rearrangement to 2-(substituted phenyl)-4,4,6,6-tetrasubstituted cycloalkanone is by the use of Lewis acid, such as boron or aluminum.

(c) Ethynylating is accomplished at room temperature in a nonprotic solvent, such as ether, THF and DME.

(d and e) Dehydration of the hydroxy trimethylsilyl-acetylene is preferably accomplished in hot, nonprotic solvent, such as ether, THF and DME under neutral conditions such as by using the Burgess Reagent or Martin sulfurane. Dehydration may also be accomplished under non-neutral conditions in a protic solvent or mineral acid. Removal of the trimethylsilyl group may be done with fluoride anion in acetic acid buffer.

(f) A strong base to form the acetylenic anion is preferably an alkyl lithium or a metallodialkyl amide.

(g and h) Metal halides include Cl, Br, I and F.

(i) The substituted heptynoate to methyl [3R]-7-(substituted phenyl)-4,4,6,6-tetrasubstituted cycloalken-1-yl]-5-oxo-3-(t-butyldimethylsilyl)oxy-hept-6-en-oate is accomplished by hydrogen reduction at room temperature and elevated pressure in the range of 10–50 psi. The same may also be done in the presence of a catalyst, such as, palladium or platinum.

(j) Isomerization takes place in the presence of iodine.

(k) Removal of silyl ether may be done by hydrolisis using mineral acids or a fluoride anion.

(l) Reduction of the β-hydroxy keto-ester may be done by using a Lewis acid, such as triethylborane or $AlCl_3$ in a nonprotic solvent at low temperature.

(m) Hydrolyzing of the diol ester is accomplished in an aqueous base at room temperature.

(n) Lactonizing the diol acid is preferably accomplished at room temperature using alkyl chloroformate and an alkyl base in a non-protic solvent. Lactonizing may also be done by heating the diol acid at a temperature of about 90° to 120° C. in a non-protic solvent, such as toluene.

The starting material and reagents are obtainable from chemical supply companies such as Aldrich Chemical Co. or may be synthesized in accordance with methods known in the art.

The example that follows illustrates in detail the synthesis of a compound of formula IV wherein the steps correspond to the steps shown in Scheme II.

In the example, unless otherwise noted, materials were obtained from commercial suppliers and used without further purification. Melting points are uncorrected. $^1H$ NMR spectra were determined with FT spectrometers operating at 270 or 300 MHz. All NMR spectra were determined with $C_6D_6$ as the solvent. Chemical shifts are expressed in ppm downfield from internal tetramethylsilane. Significant $^1H$-NMR data are tabulated in order: multiplicity (s, singlet; d, doublet; t, triplet; q, quarter; p, pentet; m, multiplet), number of protons, coupling constant(s) in hertz. Flash chromatography was done with Baker silica gel 40 μm. High Pressure Liquid Chromatography (HPLC) was done with a Rainin gradient autoprep liquid chromatography system using an 8μ-dynamax silica column.

EXAMPLE 1

[4R,6S,(E)]-[-(+)-6-[2-[2-(4-FLUORO-3-METHYL-PHENYL)-4,4,6,6-TETRAMETHYL-1-CYCLOHEXEN-1-YL]-ETHENYL]-TETRAHYDRO-4-HYDROXY-2H-PYRAN-2-ONE

Step A:
2-(4-fluoro-3-methylphenyl)-4,4,6,6-tetramethyl-1-epoxycyclohexane (2)

A solution of meta-chloroperbenzoic acid (20 g, 90 mmol) in 250 ml of $CH_2Cl_2$ is added dropwise to a cooled (0° C.) solution of 1-fluoro-2-methyl-4-(3,3,5,5-tetramethylcyclohex-1-en-1-yl)benzene (15 g, 61 mmol) and $K_2HPO_4$ (21 g, 90 mmol) in dry $CH_2Cl_2$ (100 ml). The resulting milky solution is stirred at room temperature for 14 hours, filtered and washed successively with 5% cold NaOH (2×50 ml), $H_2O$ (2×50 ml) and brine (75 ml). The $CH_2Cl_2$ fraction is dried ($MgSO_4$), and the solvent is removed under reduced pressure to provide 14 g (88%) of 2-(4-fluoro-3-methylphenyl)-4,4,6,6-tetramethyl-1-epoxycyclohexane: $^1H$ NMR δ=0.9 (s,6), 0.95 (s,3), 1.1 (s,3), 1.15 (q,2), 1.85 (AB-q, 2), 2.1 (s,3), 2.55 (s,1), 6.85 (t,1), 7.1 (t,1), 7.25 (dd,1).

Step B:
2-(4-fluoro-3-methylphenyl)-4,4,6,6-tetramethylcyclohexanone (3)

To a cooled solution (0° C.) of the epoxide from Example 1, Step A above (32.7 g, 125 mmol) in benzene (200 ml) is added dropwise 7.6 ml $BF_3 \cdot OEt_2$ (62 mmol). The cooling bath is removed and the reaction mixture warmed to room temperature and stirred for 2 hours. The benzene is removed under reduced pressure and provides a residue which is dissolved in ether (300 ml)

and washed with saturated ammonium chloride. The ether layer is concentrated under reduced pressure to provide 26 g (80%) of 2-(4-fluoro-3-methylphenyl)-4,4,6,6-tetramethylcyclohexanone. The ketone is recrystallized from pentane to give a white solid; m.p. 63°-64° C.: $^1$H NMR δ=1.05 (s,3), 1.1 (s,3), 1.3 (s,3), 1.32 (s,3), 1.75 (s,2), 2.0 (q,2), 2.3 (s,3), 3.95 (dd,1), 6.95 (m,3).

Step C:
1-((trimethylsilyl)ethynyl)-2-(4-fluoro-3-methyl-phenyl)-4,4,6,6-tetramethylcyclohexan-1-ol (4)

To a cooled solution (0° C.) of TMS-acetylene (25 g, 250 mmol) in 500 ml THF is added n-BuLi (100 ml of 2.5M THF solution, 250 mmol) dropwise. The solution is stirred at 0° C. for ½ hour and warmed to room temperature for 2½ hours. The reaction mixture is cooled to 0° C. and the ketone from Example 1, Step B above (43.7 g, 167 mmol) is added. After 14 hours the reaction mixture is diluted with ether and washed with saturated ammonium chloride solution. The ether fraction is dried over MgSO$_4$. Removal of the solvent under reduced pressure provides 58 g (97%) of the hydroxy acetylene. Purification by silica gel chromatography (5% ethyl acetate/hexane) provides 55 g (92%) of an approximate 4:1 ratio of 1-((trimethylsilyl)ethynyl)-2-(4-fluoro-3-methylphenyl)-4,4,6,6-tetramethyl-cyclohexan-1-ol as a white solid; m.p. 76°-78° C.: $^1$H NMR δ= −0.5, 0.0 (s,9), 0.75, 0.8 (s,3), 0.85, 0.9 (s,3), 0.95, 1.0 (s,3), 1.3 (m,2), 1.4 (m,2), 1.9 (t,1), 2.05, 2.1 (s,3), 2.9, 2.95 (d,1), 6.7 (t,1), 7.0 (m,2).

Step D:
1-((trimethylsilyl)ethynyl)-2-(4-fluoro-3-methyl-phenyl)-4,4,6,6-tetramethylcyclohexene (5)

To a solution of the hydroxy acetylene from Example 1, Step C above (20 g, 55.5 mmol) in acetonitrile (250 ml) is added 20 g (83 mmol) of Burgess reagent. The reaction mixture is heated at reflux for 14 hours, cooled to room temperature and diluted with H$_2$O (1 L). The aqueous solution is extracted with ether and the combined ether layers are washed with H$_2$O. The ether fraction is dried over MgSO$_4$ and the solvent is removed under reduced pressure. Purification by silica gel chromatography (100% hexane) provides 12.7 g (67%) of 1-((trimethylsilyl)ethynyl)-2-(4-fluoro-3-methylphenyl)-4,4,6,6-tetramethylcyclohexene as an oil: $^1$H NMR δ=0.0 (s,9), 0.95 (s,6), 1.15 (s,6), 1.4 ((s,2), 2.1 (s,2), 2.2 (s,3), 6.85 (t,1), 7.25 (m,2).

Step E:
1-(ethynyl)-2-(4-fluoro-3-methylphenyl)-4,4,6,6-tetramethyl-1-cyclohexene (6)

To a solution of the product from Example 1, Step D above (5 g, 14.6 mmol), and acetic acid (1.3 ml, 21.9 mmol) in THF (15 ml) at 0° C. is added tetrabutylammonium fluoride in THF (1M, 21.9 ml, 21.9 mmol). The resulting solution is stirred for 12 hours at room temperature, diluted with ether and washed with saturated ammonium chloride solution. The ether fraction is dried over MgSO$_4$, and the solvent is removed under reduced pressure. Purification by silica gel chromatography (100% hexane) provides 3.9 g (98%) of 1-(ethynyl)-2-(4-fluoro-3-methylphenyl)-4,4,6,6-tetramethyl-1-cyclohexene: $^1$H NMR δ=1.0 (s,6), 1.22 (s,6), 1.45 (s,2), 2.15 (s,2), 2.25 (s,3), 2.75 (s,1), 6.95 (t,1), 7.15 (m,2).

Preparation of:
(3S)-[(tert-butyldimethylsilyl)oxy]-4-butanoyl chloride (8)

A mixture of LiH (0.16 g, 20 mmol) in ether (10 ml) at 0° C. is stirred for 15 minutes and methyl-3-(R)-hydroxypentanedioate (prepared as described by Heathcock and Theisen *J. Org. Chem.* 1988, 53, 2374) (5.4 g, 20 mmol) in benzene (10 ml) is added. The resulting solution is stirred for 20 minutes and oxalyl chloride (26 ml, 30 mmol) is added. The reaction mixture is stirred at 0° C. for ½ an hour and then at room temperature for 2 hours. The mixture is filtered and concentrated under reduced pressure to provide 4.9 g (85%) of (3S)-[(tert-butyldimethylsilyl)oxy]-4-butanoyl chloride: $^1$H NMR δ=0.0 (s,3), 0.1 (s,3), 0.95 (s,9), 2.0–2.3 (m,2), 2.5–2.8 (m,2), 3.3 (s,3), 4.5 (p,1).

Step F,G,H: Methyl
[3R]-7-[2-(4-fluoro-3-methylphenyl)-4,4,6,6-tetramethyl-cyclohex-1-en-1-yl]-5-oxo-3-[(tert-butyldimethylsilyl)oxy]hept-6-yn-oate (9)

To a solution of the product from Example 1, Step E above (1.2 g, 4.4 mmol) in ether (10 ml) at 0° C. is added dropwise n-BuLi in THF (1.6 ml, 4.0 mmol) and after 15 minutes is warmed to room temperature. After 2 hours the reaction mixture is cooled to −10° C. and manganese iodide (1.4 g, 4.4 mmol) is added. After 1 hour the optically active acid chloride (compound 8 from above) (1.6 g, 5.5 mmol) in ether (5 ml) is added dropwise. The reaction mixture is stirred at −10° C. for 12 hours and diluted with ether and saturated ammonium chloride solution. The ether layer is dried (MgSO$_4$) and concentrated under reduced pressure. Purification by silica gel chromatography (3% ethyl acetate/hexane) provides methyl [3R]-7-[2-(4-fluoro-3-methylphenyl)-4,4,6,6-tetramethylcyclohex-1-en-1-yl]-5-oxo-3-[(tert-butyldimethylsilyl)oxy]hept-6-yn-oate, 2.1 g (90%): $^1$H NMR δ=0.0 (s,6), 0.78 (s,6), 0.82 (s,9), 1.2 (s,6), 1222 (s,2), 1.88 (s,2), 2.1 (s,3), 2.2–2.65 (m,4), 3.25 (s,3), 4.65 (p,1), 6.8–7.1 (m,3).

Step I: Methyl
[3R]-(Z)-7-[2-(4-fluoro-3-methylphenyl)-4,4,6,6-tetramethylcyclohex-1-en-1-yl]-5-oxo-3-[(tert-butyldimethylsilyl)oxy]hept-6-en-oate (10)

A mixture of the product from Example 1, Step F,G,H above (0.5 g, 0.95 mmol) and Pd(OH)$_2$ (0.1 g) in 25% ethyl acetate in hexanes (30 ml) is hydrogenated at 20 psi for 10 hours. The reaction mixture is filtered and removal of the solvent under reduced pressure gives 0.42 g (85%) of methyl [3R]-(Z)-7-[2-(4-fluoro-3-methylphenyl)-4,4,6,6-tetramethylcyclohex-1-en-1-yl]-5-oxo-3-[(tert-butyldimethylsilyl)oxy]hept-6-en-oate. This material is used directly in the isomerization step: $^1$H NMR δ=0.05 (s,3), 0.1 (s,3), 0.7 (s,9), 0.9–1.0 (m,12), 1.2 (s,3), 1.9 (s,2), 2.0 (s,3), 1.9–2.2 (m,4), 3.1 (s,3), 4.45 (p,1), 5.5 (d,1,J=12), 7.1–7.3 (m,3).

Step J: Methyl
[3R]-(E)-7-[2-(4-fluoro-3-methylphenyl)-4,4,6,6-tetramethyl-1-yl]-5-oxo-3-(tert-butyldimethylsilyloxy)-hept-6-en-oate (11)

A solution of the product from Example 1, Step I above (0.3 g, 0.57 mmol) in CHCl$_3$ (15 ml) with a catalytic amount of iodine is heated to 55° C. for 14 hours. The reaction mixture is diluted with CHCl$_3$ and washed with 25% aqueous sodium thiosulfate, H$_2$O and brine.

The CHCl₃ layer is concentrated under reduced pressure to provide a residue which was purified by HPLC using ethyl acetate/hexane to give 0.26 g (89%) of methyl [3R]-(E)-7-[2-(4-fluoro-3-methylphenyl)-4,4,6,6-tetramethyl-1-cyclohexen-1-yl]-5-oxo-3-(tert-butyl-dimethylsilyloxy)hept-6-en-oate: $^1$H NMR $\delta$=0.0 (s,3), 0.05 (s,3), 0.8 (s,9), 1.1 (s,6), 1.25 (s,6), 1.45 (s,2), 1.5 (s,2), 2.2 (s,3), 2.3–2.6 (m,4), 3.65 (s,3), 4.5 (p,1), 6.0 (d,1,J=16.8), 6.8–7.2 (m,3), 7.2 (d,1,J=16.5).

Step K: Methyl [3R]-(E)-7-[2-(4-fluoro-3-methylphenyl)-4,4,6,6-tetramethyl-1-cyclohexen-1-yl]-5-oxo-3-hydroxyhept-6-en-oate (12)

To a cooled solution (0° C.) of the product from Example 1, Step J above (0.2 g, .377 mmol) in CH₃CN (2 ml) is added 6.0 ml of 1:19 solution of 40% aqueous HF in CH₃CN. The resulting solution is stirred at room temperature for 2 hours, diluted with CH₂Cl₂ and washed with saturated aqueous NaHCO₃ and brine. The combined organic fractions are dried over MgSO₄ and the solvent is removed under reduced pressure to provide a yellow oil. The crude hydroxy-ketone is purified by silica gel chromatography (15% ethyl acetate/hexane) to obtain 0.15 g (95%) of methyl [3R]-(E)-7-[2-(4-fluoro-3-methylphenyl)-4,4,6,6-tetramethyl-1-cyclohexen-1-yl]-5-oxo-3-hydroxyhept-6-en-oate: $^1$H NMR $\delta$=0.8–1.1 (m,16), 2.0 (s,2), 2.1 (s,3), 2.3–2.6 (m,4), 3.3 (s,3), 4.8 (m,1), 6.2 (d,1,J=16.8), 6.7–7.1 (m,3), 7.4 (d,1,J=16.6).

Step L: Methyl [3R,5S,(E)]-7-[2-(4-fluoro-3-methylphenyl)-4,4,6,6-tetramethyl-1-cyclohexen-1-yl]-3,5-dihydroxyhept-6-en-oate (13)

A solution of the product from Example 1, Step K above (0.2 g, 0.48 mmol) in THF (5 ml) is treated with a solution of triethylborane (1M in THF, 0.7 ml, 0.7 mmol). The resulting solution is stirred at room temperature for 5 minutes, cooled to −78° C. and treated with NaBH₄ (0.022 g, 0.58 mmol), followed by dropwise addition of methanol (5 ml) over a 30 minute period. The reaction mixture is stirred for ½ hour at −78° C. and then slowly warmed over 30 minutes to −60° C. The reaction mixture is quenched at −60° C. by slow addition of 30% hydrogen peroxide (10 ml). The reaction mixture is warmed to room temperature and stirred for ½ hour, diluted with EtOAc and is then washed with saturated ammonium chloride solution. The ethyl acetate layer is dried over MgSO₄ and concentrated under reduced pressure to give a residue which is purified by silica gel chromatography and provides 0.18 g (90%) of methyl [3R,5S,(E)]-7-[2-(4-fluoro-3-methylphenyl)-4,4,6,6-tetramethyl-1-cyclohexen-1-yl]-3,5-dihydroxyhept-6-en-oate.

Step M: [3R,5S,(E)]-7-[2-(4-fluoro-3-methylphenyl)-4,4,6,6-tetramethyl-1-cyclohexen-1-yl]-3,5-dihydroxyhept-6-enoic acid (14)

A solution of the product from Example 1, Step L above (0.2 g, 0.48 mmol) in CH₃CN (4 ml) and 10% NaOH (0.2 ml, 0.5 mmol) is stirred for ½ an hour and diluted with ethyl acetate. The ethyl acetate layer is dried (MgSO₄) and concentrated under reduced pressure to provide [3R,5S,(E)]-7-[2-(4-fluoro-3-methylphenyl)-4,4,6,6-tetramethyl-1-cyclohexen-1-yl]-3,5-dihydroxyhept-6-enoic acid.

Step N: [4R,6S,(E)]-(+)-6-[2-[2-(4-fluoro-3-methylphenyl)-4,4,6,6-tetramethyl-1-cyclohexen-1-yl]ethenyl]-tetrahydro-4-hydroxy-2H-pyran-2-one (15)

To a cooled solution (0° C.) of the product from Example 1, Step M above (0.3 g, 0.75 mmol), triethylamine (0.1 ml, 0.74 mmol) in CH₂Cl₂ (4 ml) is added ethyl chloroformate (0.07 ml, 0.74 mmol) in CH₂Cl₂ (1 ml). The reaction mixture is stirred until completion, poured into ice/H₂O and extracted with CH₂Cl₂. The organic layer is dried (MgSO₄) and concentrated under reduced pressure to give a residue which is purified by silica gel chromatography (15% ethyl acetate/hexane) and provides 0.2 g (75%) of [4R,6S,(E)]-(+)-6-[2-[2-(4-fluoro-3-methylphenyl)-4,4,6,6-tetramethyl-1-cyclohexen-1-yl]ethenyl]-tetrahydro-4-hydroxy-2H-pyran-2-one. HPLC analysis of this material shows it to be >98% enantiomeric excess.

The intermediate compounds of the present invention are useful in the preparation of compounds of Formula IV which are useful as hypocholesterolemic or hypolipidemic agents by virtue of their ability to inhibit the biosynthesis of cholesterol through inhibition of the enzyme HMG-CoA reductase. Having such ability, the compounds of Formula IV are incorporated into pharmaceutically acceptable carriers and administered to a patient in need of such cholesterol biosynthesis inhibition orally or parenterally. Such pharmaceutical formulations to contain at least one compound according to the invention.

Suitable carriers include diluents or fillers, sterile aqueous media and various non-toxic organic solvents. The compositions may be formulated in the form of tablets, capsules, lozenges, trochees, hard candies, powders, aqueous suspensions, or solutions, injectable solutions, elixirs, syrups and the like and may contain one or more agents selected from the group including sweetening agents, flavoring agents, coloring agents and preserving agents in order to provide a pharmaceutically acceptable preparation.

The particular carrier and the ratio of active compound to carrier are determined by the solubility and chemical properties of the compounds, the particular mode of administration and standard pharmaceutical practice. For example, excipients such as lactose, sodium citrate, calcium carbonate and dicalcium phosphate and various disintegrants such as starch, alginic acid and certain complex silicates, together with lubricating agents such as magnesium stearate, sodium lauryl sulphate and talc, can be used in producing tablets. For a capsule form, lactose and high molecular weight polyethylene glycols are among the preferred pharmaceutically acceptable carriers.

Where aqueous suspensions for oral use are formulated, the carrier can be emulsifying or suspending agents. Diluents such as ethanol, propylene glycol, and glycerin and their combinations can be employed as well as other materials.

For parental administration, solutions or suspensions of these compounds in aqueous alcoholic media or in sesame or peanut oil or aqueous solutions of the soluble pharmaceutically acceptable salves can be employed.

The dosage regiment in carrying out the methods of this invention is that which insures maximum therapeutic response until improvement is obtained and thereafter the minimum effective level which gives relief. Doses may vary, depending on the age, severity, body weight and other conditions of the patients but are ordinarily in the area of 5 mg/kg to 500 mg/kg of body weight in oral administration; such may, of course, be given in two to four divided doses. With other forms of administration equivalent or adjusted doses will be administered depending on the route of administration.

The utility of the claimed compounds is measured by the test methods described in U.S. Pat. No. 4,863,957, which is incorporated herein by reference.

Result on the compound of Example 1 tested by the described methods showed that the resolved (+) enantiomer possess enhanced properties in comparison with, and is significantly more potent in inhibiting cholesterol synthesis, than the unresolved (±) enantiomer.

What is claimed is:

1. A compound of formula I

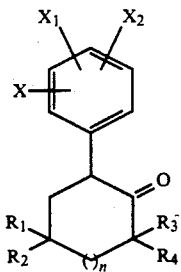

Formula I wherein
$X$, $X_1$ and $X_2$ are independently H, F, Cl, Br, OH, $CF_3$, alkyl, alkoxy, aryl, $NO_2$, NH(CO)R, $N(R)_2$ or $S(O)_m R$;
$R_1$ and $R_2$ are independently H, alkyl, aryl, OR, F, Cl or Br;
$R_3$ and $R_4$ taken together can form a spirocyclic ring having 4 to 6 carbon atoms;
R is H or lower alkyl; m is 0–2; and
n is 0–2.

2. The compound which is 2-(4-fluoro-3-methylphenyl)-4,4,6,6-tetramethyl-1-cyclohexanone.

* * * * *